(12) United States Patent
Hamada et al.

(10) Patent No.: US 8,557,020 B2
(45) Date of Patent: Oct. 15, 2013

(54) COMPOUND, METAL EXTRACTANT, AND APPLICATION OF THE SAME

(75) Inventors: Fumio Hamada, Akita (JP); Chun-Bin Li, Akita (JP); Yoshihiko Kondo, Akita (JP)

(73) Assignees: Dowa Holdings Co., Ltd., Tokyo (JP); Akita University, Akita (JP)

( * ) Notice: Subject to any disclaimer, the term of this patent is extended or adjusted under 35 U.S.C. 154(b) by 359 days.

(21) Appl. No.: 13/038,751

(22) Filed: Mar. 2, 2011

(65) Prior Publication Data
US 2011/0247459 A1 Oct. 13, 2011

(30) Foreign Application Priority Data
Apr. 13, 2010 (JP) .................... 2010-092533

(51) Int. Cl.
B01D 11/04 (2006.01)
C07F 9/50 (2006.01)
C22B 34/14 (2006.01)
C22B 11/00 (2006.01)

(52) U.S. Cl.
USPC ............. 75/632; 75/612; 75/633; 210/635; 568/13

(58) Field of Classification Search
USPC ............. 75/743, 744, 612, 632, 633; 210/634–655; 568/13
See application file for complete search history.

(56) References Cited

U.S. PATENT DOCUMENTS
2010/0180730 A1* 7/2010 Nagai et al. ............ 75/744

FOREIGN PATENT DOCUMENTS
JP 2004332041 A * 11/2004 .......... C22B 11/00
JP 2007-239066 9/2007
JP 2007-239088 9/2007

OTHER PUBLICATIONS
Selective Extraction of Precious Metal from Automotive Catalyst Residue by Diphenylphosphine TC4A propyl ether, Akita University Venture Business Laboratory Work Shop, (March, H22), Japan Fiscal Year (JFL) H21, 2009.

* cited by examiner

Primary Examiner — Kaj K Olsen
Assistant Examiner — Jared Wood
(74) Attorney, Agent, or Firm — Carmody & Torrance LLP

(57) ABSTRACT

A compound represented by General Formula (1) below,

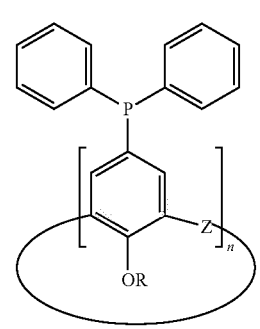

General Formula (1)

where R denotes a C1-C10 hydrocarbon group, Z denotes any one of a sulfide group, a sulfinyl group and a sulfonyl group, and n denotes an integer of 4 to 8 is described. A method for extracting metals and a metal recovery method using a metal extractant comprising the compound represented by General Formula (1) are also described.

9 Claims, 1 Drawing Sheet

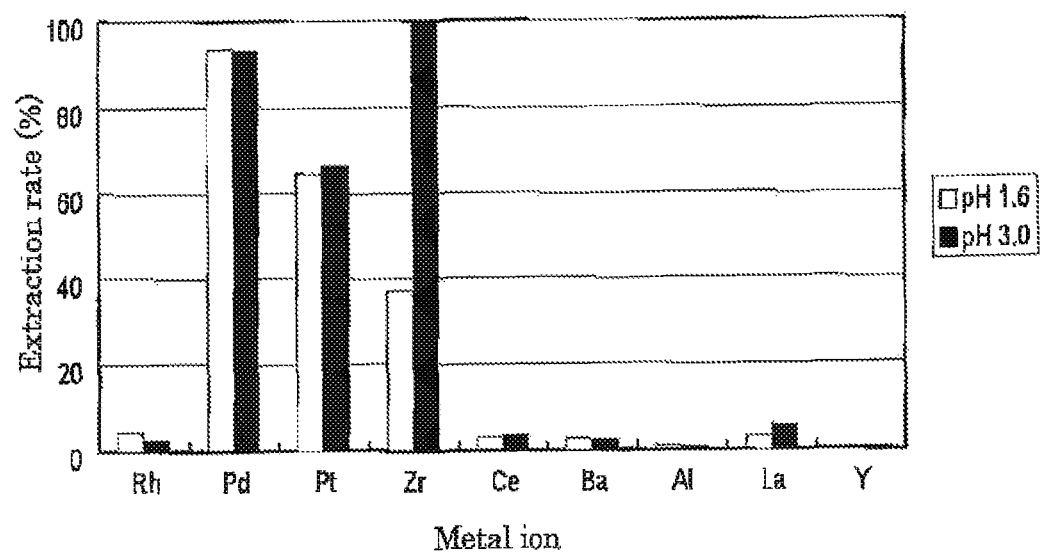

COMPOUND, METAL EXTRACTANT, AND APPLICATION OF THE SAME

RELATED APPLICATION DATA

This application claims the benefit of Japanese Application No. 2010-092533, filed Apr. 13, 2010, the subject matter of which is incorporated by reference in its entirety.

BACKGROUND OF THE INVENTION

1. Field of the Invention

The present invention relates to a new compounds a metal extractant including the new compound; a method for extracting zirconium or at least one of palladium and platinum, using the metal extractant; a method for recovering at least one of palladium and platinum and recovering zirconium, using the metal extractant; and a method for separately extracting palladium and platinum, using the metal extractant.

2. Description of the Related Art

Metals such as cobalt (Co), titanium (Ti), nickel (Ni), vanadium (V), chromium (Cr), manganese (Mn), zinc (Zn), yttrium (Y), zirconium (Zr), hafnium (bat), niobium (Nb), cadmium (Cd), lanthanum (La), cerium (Ce), neodymium (Nd), europium (Eu), terbium (Tb), mercury (Hg), uranium (U), platinum (Pt), palladium (Pd), rhodium (Rh), ruthenium (Ru), iridium (Ir), osmium (Os), barium (Ba) and aluminum (Al) are included, in the 31 minerals defined by the Rare Metal Division of the Mineral Resources Subcommittee, Advisory Committee for Natural Resources and Energy of Ministry of Economy, Trade and Industry, and these metals are indispensable to our lives and are used for a variety of products including present-day precision instruments, such as automotive catalysts, fuel cells and ultrahigh-strength magnets.

Among these metals, palladium and platinum are used as materials for precision instruments, dental materials, etc. and zirconium is used for piezoelectric elements, condensers, etc. Palladium, platinum and zirconium are metals that are present in the smallest amounts in the Earth's crust, and thus their prices have been increasing amid the recent competition among countries to procure resources. Accordingly, in view of stable supply of resources and protection of the environment, methods for recycling palladium, platinum and zirconium have been proposed.

Among the methods for recycling palladium, platinum and zirconium, there is, for example, a method wherein an extractant for extracting palladium, platinum and zirconium is added to an aqueous solution containing palladium, platinum and zirconium so as to extract the palladium, the platinum and the zirconium, and a variety of extractants for this sort of purpose have been developed and utilized (refer to Japanese Patent Application Laid-Open (JP-A) Nos. 2007-239066 and 2007-239088).

However, the selectivity with which any of palladium, platinum and zirconium is extracted and the extraction rate thereof are not satisfactory enough; accordingly, provision of an extractant capable of extracting any of these with higher selectivity and at a higher extraction rate is being demanded, and provision of an extractant having selectivity for platinum that has a particularly wide range of uses, among the above-mentioned metals, is being highly demanded.

Thus, in reality, swift development of a new metal extractant capable of selectively extracting any of palladium, platinum and zirconium is being strongly demanded.

BRIEF SUMMARY OF THE INVENTION

The present invention is aimed at solving the problems in related art and achieving the following object. An object of the present invention is to provide: a new compound with which any of palladium, platinum and zirconium can be selectively and highly efficiently extracted; a metal extractant including the new compound; a method for selectively and highly efficiently extracting zirconium or at least one of palladium and platinum, using the metal extractant; a method for recovering at least one of palladium and platinum and recovering zirconium, using the metal extractant; and a method for separately extracting palladium and platinum, using the metal extractant.

As a result of carrying out earnest examinations in an attempt to solve the problems, the present inventors have obtained the following findings. The present inventors have found that a new compound of the present invention is suitably utilizable for a metal extractant, and that the metal extractant makes it possible to selectively extract zirconium or at least one of palladium and platinum with high efficiency, to recover at least one of palladium and platinum and recover zirconium with high efficiency, and to separately extract palladium and platinum with high efficiency; and these findings have led to completion of the present invention.

The present invention is based upon the findings of the present inventors, and means for solving the problems are as follows.

<1> A compound represented by General Formula (1) below,

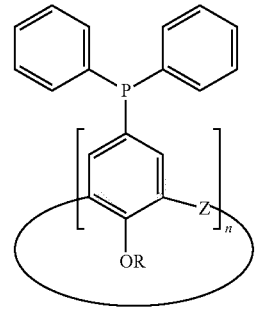

General Formula (1)

where R denotes a C1-C10 hydrocarbon group, Z denotes any one of a sulfide group, a sulfonyl group and a sulfonyl group, and n denotes an integer of 4 to 8.

<2> The compound according to <1>, wherein R denotes a propyl group.

<3> The compound according to <1> or <2>, wherein Z denotes a sulfide group.

<4> The compound according to any one of <1> to <3>, wherein n denotes 4.

<5> A metal extractant including the compound according to any one of <1> to <4>.

<6> A method for extracting at least one of palladium and platinum, including: adjusting a pH of an aqueous solution, which contains at least one of palladium and platinum, at 25° C. to less than 7; and bringing an organic phase, which contains at least the metal extractant according to <5>, into contact with the aqueous solution, whose pH has been adjusted and which contains at least one of the palladium and the platinum, and extracting at least one of the palladium and the platinum into the organic phase.

<7> A method for extracting zirconium, including; adjusting a pH of an aqueous solution, which contains zirconium, at 25° C. to less than 7; and bringing an organic phase, which contains at least the metal extractant according to <5>, into contact with the aqueous solution, whose pH has been adjusted and which contains the zirconium, and extracting the zirconium into the organic phase.

<8> A metal recovering method including: adjusting a pH of an aqueous solution, which contains zirconium and at least one of palladium and platinum, at 26° C. to less than 3 as a first pH adjusting step; bringing an organic phase, which contains at least the metal extractant according to <5>, into contact with the aqueous solution, whose pH has been adjusted in the first pH adjusting step, and extracting at least one of the palladium and the platinum into the organic phase as a first extracting step; recovering at least one of the palladium and the platinum from the organic phase obtained in the first extracting step as a first recovering step; adjusting the pH of the aqueous solution, which has undergone the first recovering step and contains the zirconium, to 3 or greater, but less than 7 as a second pH adjusting step; bringing an organic phase, which contains at least the metal extractant according to <5>, into contact with the aqueous solution, whose pH has been adjusted in the second pH adjusting step and which contains the zirconium, and extracting the zirconium into the organic phase as a second extracting step; and recovering the zirconium from the organic phase obtained in the second extracting step as a second recovering step.

<9> A method for separately extracting palladium and platinum, including: adjusting a pH of an aqueous solution, which contains palladium and platinum, at 25° C. to less than 7; bringing a first organic phase, which contains at least an extractant having selectivity for the palladium, into contact with the aqueous solution, whose pH has been adjusted and which contains the palladium and the platinum, and extracting the palladium into the first organic phase; and bringing a second organic phase, which contains at least the metal extractant according to <5>, into contact with the aqueous solution, which has undergone the extraction of the palladium and contains the platinum, and extracting the platinum into the second organic phase.

The present invention makes it possible to solve the problems in related art and achieve the object of providing: a new compound with which any of palladium, platinum and zirconium can be selectively and highly efficiently extracted; a metal extractant including the new compound; a method for selectively and highly efficiently extracting zirconium or at least one of palladium and platinum, using the metal extractant; a method for recovering at least one of palladium and platinum and recovering zirconium, using the metal extractant and a method for separately extracting palladium and platinum, using the metal extractant.

BRIEF DESCRIPTION OF THE DRAWING

FIG. 1 is a graph exemplarily showing extraction results concerning Examples 1 to 3. In this graph, white columns show results of extraction performed at a pH of 1.6, and black columns show results of extraction performed at a pH of 3.0.

DETAILED DESCRIPTION OF THE INVENTION (New Compound)

A new compound of the present invention is a cyclic phenol sulfide derivative represented by General Formula (1) below,

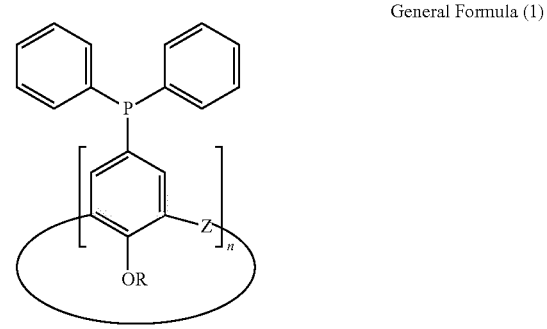

General Formula (1)

In General Formula (1), R denotes a C1-C10 hydrocarbon group.

Also in General Formula (1), Z denotes any one of a sulfide group, a sulfinyl group and a sulfonyl group; it is particularly preferred that Z denote a sulfide group in view of facilitation of synthesis.

Also in General Formula (1), n denotes an integer of 4 to 8; it is preferred that n denote 4, 6 or 8, particularly 4, in view of facilitation of synthesis.

The C1-C10 hydrocarbon group is not particularly limited and may be suitably selected according to the intended purpose, and it is, for example, a straight-chain or branched-chain alkyl group. Also, instead of denoting a hydrocarbon group, R may denote a carbonyl group.

The alkyl group is not particularly limited and may be suitably selected according to the intended purpose, provided that it has 1 to 10 carbon atoms. Examples thereof include a methyl group, an ethyl group, an n-propyl group, an isopropyl group, an n-butyl group, an isobutyl group, a t-butyl group, an n-pentyl group and an n-hexyl group. Among these, C1-C5 alkyl groups (e.g., a methyl group, an ethyl group, a propyl group, a butyl group and a pentyl group), particularly C1-C3 alkyl groups (e.g., a methyl group, an ethyl group and a propyl group), are preferable in view of facilitation of synthesis.

Specific examples of the compound represented by General Formula (1) above include p-tert-butylthiacalix[4]arene (hereinafter referred to as "TC4A") represented by Structural-Formula (1) below; it should, however, be noted that the compound of the present invention is not limited thereto,

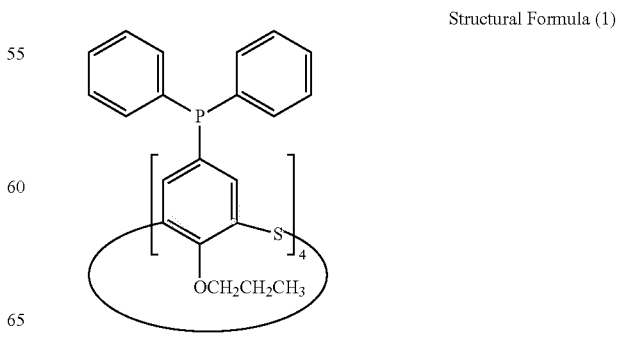

Structural Formula (1)

The production method of the compound represented by General Formula (1) above is not particularly limited and may be suitably selected according to the intended purpose. For example, the cyclic sulfide derivative can be produced as follows: an alkylphenol as a starting material is reacted with sulfur as a simple substance in the presence of an alkali metal reagent or an alkaline earth metal reagent to obtain a cyclic phenol sulfide with a plurality of, preferably four, alkylphenols linked together by sulfide bond(s); subsequently, the para position (fourth position) of each phenol with respect to the hydroxyl group is halogenated, then the hydroxyl group of each phenol is replaced with a C1-C10 hydrocarbon group, and the halogen at the para position (fourth position) is replaced with diphenylphosphine.

The structure of the compound represented by General Formula (1) above can be identified by analysis of an elemental disposition in accordance with NMR spectroscopy and/or JR spectroscopy, or by elemental analysis and/or molecular weight measurement, for example.

<Uses>

The new compound can be suitably used to extract palladium, platinum and zirconium in particular among metals and can be suitably utilized for the present invention's metal extractant, method for extracting at least one of palladium and platinum, method for extracting zirconium, metal recovering method and method for separately extracting palladium and platinum, which will be later described.

(Metal Extractant)

A metal extractant of the present invention includes the above-mentioned compound of the present invention, represented by General Formula (1) above, and may, if necessary, include other components as well.

The metal extractant is advantageous in that it is capable of selectively extracting palladium, platinum and zirconium among metals.

<Compound>

The amount of the compound represented by General Formula (1) above, included in the metal extractant, is not particularly limited and may be suitably selected according to the intended purpose. Also, the metal extractant may be composed solely of the compound represented by General Formula (1) above.

<Other Components>

The above-mentioned other components are not particularly limited and may be suitably selected according to the intended purpose, and examples thereof include an antioxidant.

<Usage>

The usage of the metal extractant is not particularly limited and may be suitably selected according to the intended purpose. Preference is given to a method of dissolving the metal extractant in solvent and then bringing the obtained solution into contact with an aqueous solution which contains any of palladium, platinum and zirconium.

The solvent is not particularly limited and may be suitably selected according to the intended purpose, and examples thereof include chloroform, toluene and dichloromethane. These may be used individually or in combination. Among these, chloroform is preferable as the solvent.

The metal extractant may be used solely or in combination with other metal extractant(s). In the case where the metal extractant is used in combination with the other metal extractant(s), the other metal extractant(s) preferably has/have suitable selectivity for metal(s).

<Uses>

The metal extractant can be suitably used to extract palladium, platinum and zirconium in particular among metals and can be suitably utilized, for example, for the present invention's method for extracting at least one of palladium and platinum, method for extracting zirconium, metal recovering method and method for separately extracting palladium and platinum, which will be described later.

(Method for Extracting at Least One of Palladium and Platinum)

A method of the present invention for extracting at least one of palladium and platinum includes a pH adjusting step and an extracting step and may, if necessary, include other steps as well.

<pH Adjusting Step>

The pH adjusting step is a step of adjusting the pH of an aqueous solution, which contains at least one of palladium and platinum, at 25° C.

The pH of the aqueous solution at 25° C. is less than 7; it is preferred that the pH be less than 5, more preferably less than 3, particularly preferably in the range of 1 to 2, in view of the fact that high selectivity for at least one of the palladium and the platinum is exhibited. When the pH is 7 or greater, metal(s) in the aqueous phase may precipitate and thus it may be impossible to selectively extract at least one of the palladium and the platinum.

Here, the term "high selectivity" means that at least one of the palladium and the platinum can be extracted at an extraction rate of 60% or above.

The method of measuring the pH is not particularly limited and may be suitably selected according to the intended purpose, and examples thereof include a measuring method which uses a pH meter (such as pH METER D-51, manufactured by HORIBA, Ltd.). Note that if the pH of the aqueous solution, which contains at least one of the palladium and the platinum, at 25° C. is already less than 7 when measured, the above-mentioned pH adjusting step may be omitted.

The method of adjusting the pH is not particularly limited, provided that the pH can be adjusted to a desired value, and the method may be suitably selected according to the intended purpose. Examples thereof include a method of adding an acid or an alkali to the aqueous solution containing the metal(s) to be extracted.

The acid/alkali is not particularly limited and may be suitably selected according to the intended purpose, and examples thereof include acids/alkalis commonly used for pH adjustment.

Specific examples of the acid include inorganic acids such as sulfuric acid, hydrochloric acid and nitric acid; and organic acids such as acetic acid. These may be used individually or in combination.

Specific examples of the alkali include hydroxide salts of metals such as sodium hydroxide, potassium hydroxide and calcium hydroxide; amines such as dimethylamine, trimethylamine, monoethylamine, diethylamine, triethylamine, ethylenediamine and pyridine; and ammonia-based compounds such as ammonia water, ammonium carbonate and ammonium hydrogen carbonate. These may be used individually or in combination.

<Extracting Step>

The extracting step is a step of bringing an organic phase, which contains at least the above-mentioned metal extractant of the present invention, into contact with the aqueous solution, whose pH has been adjusted and which contains at least one of the palladium and the platinum, and extracting at least one of the palladium and the platinum into the organic phase.

<<Organic Phase>>

The organic phase contains at least the metal extractant, preferably contains a solvent and may, if necessary, contain other components as well.

—Extractant—

The concentration of the metal extractant in the organic phase is not particularly limited and may be suitably selected according to the intended purpose. The concentration of the metal extractant is preferably in the range of $1\times10^{-6}$ mol/L to 1 mol/L, more preferably $1\times10^{-5}$ mol/L to $1\times10^{-2}$ mol/L, particularly preferably $1\times10^{-3}$ mol/L to $1\times10^{-2}$ mol/L. When the concentration of the metal extractant is less than $1\times10^{-6}$ mol/L, extraction of at least one of the palladium and the platinum may be difficult. When the concentration of the metal extractant is greater than 1 mol/L, an emulsion may be formed and so separation between the aqueous phase and the organic phase may be difficult.

—Solvent—

The solvent is not particularly limited, provided that it can dissolve the metal extractant, and the solvent may be suitably selected according to the intended purpose. In view of facilitation of extraction of at least one of the palladium and the platinum, the solvent is preferably a water-insoluble solvent which is not compatible with the aqueous solution (aqueous phase) containing at least one of the palladium and the platinum.

The water-insoluble solvent is not particularly limited and may be suitably selected according to the intended purpose, and examples thereof include mineral oils such as petroleum and kerosene; aliphatic hydrocarbon solvents such as hexane, heptane and octane; aromatic hydrocarbon solvents such as toluene and xylene; and halogenated solvents such as carbon tetrachloride, methylene chloride, chloroform and ethylene chloride. These may be used individually or in combination.

—Other Components—

The above-mentioned other components optionally contained in the organic phase are not particularly limited and may be suitably selected according to the intended purpose. Also, the amounts of these other components are not particularly limited and may be suitably selected according to the intended purpose.

<<Extracting Method>>

The method of bringing the organic phase into contact with the aqueous solution is not particularly limited and may be suitably selected according to the intended purpose, and examples thereof include a method of mixing a solution, which contains the organic phase, with the aqueous solution, which contains at least one of the palladium and the platinum, and shaking or stirring the mixture. By such a method, it is possible to extract at least one of the palladium and the platinum from the aqueous solution.

The speed at which the shaking is performed is not particularly limited and may be suitably selected according to the intended purpose. The speed is preferably in the range of 100 strokes/min to 800 strokes/min, more preferably 300 strokes/min to 800 strokes/min, particularly preferably 500 strokes/min to 800 strokes/min. When the speed is lower than 100 strokes/rain, it may be impossible to enable sufficient contact between the organic phase and the aqueous phase and thus impossible to extract the metal(s) satisfactorily. When the speed is higher than 800 strokes/min, an emulsion may be formed.

The length of time for which the shaking is performed is not particularly limited and may be suitably selected according to the intended purpose. The length of time is preferably in the range of 5 minutes to 30 minutes, more preferably 10 minutes to 30 minutes, particularly preferably 20 minutes to 30 minutes. When the length of time is shorter than 5 minutes, the organic phase and the aqueous phase are in contact with each other only for a short period of time and thus it may be impossible to extract the metal(s). When the length of time is longer than 30 minutes, the extraction rate does not increase, hence inefficiency.

The speed at which the stirring is performed is not particularly limited and may be suitably selected according to the intended purpose. The speed is preferably in the range of 10 rpm to 1,000 rpm, more preferably 300 rpm to 1,000 rpm, particularly preferably 800 rpm to 1,000 rpm. When the speed is lower than 10 rpm, the mixture may not be sufficiently stirred, so that sufficient contact between the organic phase and the aqueous phase may be impossible and thus the metal(s) may not be able to be extracted. When the speed is higher than 1,000 rpm, an emulsion may be formed.

The length of time for which the stirring is performed is not particularly limited and may be suitably selected according to the intended purpose. The length of time is preferably in the range of 1 hour to 24 hours, more preferably 12 hours to 24 hours, particularly preferably 20 hours to 24 hours. When the length of time is shorter than 1 hour, the organic phase and the aqueous phase are in contact with each other only for a short period of time and thus it may be impossible to extract the metal(s). When the length of time is longer than 24 hours, the extraction rate does not increase, hence inefficiency.

<Other Steps>

The above-mentioned other steps optionally included in the method for extracting at least one of palladium and platinum are not particularly limited and may be suitably selected according to the intended purpose, and examples thereof include a step of confirming, by analysis, whether or not at least one of the palladium and the platinum has been extracted.

The analysis is not particularly limited and may be suitably selected according to the intended purpose, and examples thereof include analyse is with an ICP emission analyzer or with an analyzer employing high-speed liquid chromatography, gas chromatography, ion chromatography, mass spectrometry, etc.

<Uses>

Since the method for extracting at least one of palladium and platinum enables at least one of palladium and platinum to be selectively and highly efficiently extracted, the method can be suitably used, for example, for recycling at least one of palladium and platinum in view of stable supply of resources, protection of the environment, etc.

(Method for Extracting Zirconium)

A method of the present invention for extracting zirconium includes a pH adjusting step and an extracting step and may, if necessary, include other steps as well.

<pH Adjusting Step>

The pH adjusting step is a step of adjusting the pH of an aqueous solution, which contains zirconium, at 25° C.

The pH of the aqueous solution at 25° C. is less than 7; it is preferred that the pH be less than 5, more preferably greater than 1.6 but less than 5, particularly preferably 3 or greater, but less than 5. When the pH is 1.6 or less, the extraction rate of the zirconium may be less than 50%, and so the efficiency with which the zirconium is selectively extracted may be poor. When the pH is 7 or greater, metal(s) in the aqueous phase may precipitate, which is unsuitable for extraction conditions.

Here, the term "high selectivity" means that the zirconium can be extracted at an extraction rate of 60% or above.

Note that if the pH of the aqueous solution, which contains the zirconium, at 25° C. is already less than 7 when measured, the above-mentioned pH adjusting step may be omitted.

The method of measuring the pH is not particularly limited and may be suitably selected according to the intended purpose, and examples thereof include a measuring method which uses a pH meter (such as PH METER D-51, manufactured by HORIBA, Ltd.).

For adjustment of the pH, a method of adding an acid or an alkali may be employed as in the pH adjusting step in the above-mentioned method for extracting at least one of palladium and platinum.

<Extracting Step>

The extracting step is a step of bringing an organic phase, which contains at least the above-mentioned metal extractant of the present invention, into contact with the aqueous solution, whose pH has been adjusted and which contains the zirconium, and extracting the zirconium into the organic phase.

<<Organic Phase>>

The organic phase contains at least the metal extractant, preferably contains a solvent and may, if necessary, contain other components as well.

The concentration of the metal extractant, the type of the solvent, and the above-mentioned other components are not particularly limited and may be suitably selected according to the intended purpose; for example, the organic phase may be similar to the organic phase employed in the above-mentioned method for extracting at least one of palladium and platinum.

<<Extracting Method>>

The method of bringing the organic phase into contact with the aqueous solution is not particularly limited and may be suitably selected according to the intended purpose, and examples thereof include a method similar to the method employed in the extracting step in the above-mentioned method for extracting at least one of palladium and platinum, <Other Steps>

The above-mentioned other steps optionally included in the method for extracting zirconium are not particularly limited and may be suitably selected according to the intended purpose, and examples thereof include a step of confirming, by analysis, whether or not the zirconium has been extracted.

The analysis is not particularly limited and may be suitably selected according to the intended purpose, and examples thereof include analysis with an ICP emission analyzer or with an analyzer employing high-speed liquid chromatography, gas chromatography, ion chromatography, mass spectrometry, etc.

<Uses>

Since the method for extracting zirconium enables zirconium to be selectively and highly efficiently extracted, the method can be to suitably used, for example, for recycling zirconium in view of stable supply of resources, protection of the environment, etc.

(Metal Recovering Method)

A metal recovering method of the present invention is a method for recovering at least one of palladium and platinum and also recovering zirconium, and the metal recovering method includes a first pH adjusting step, a first extracting step, a first recovering step, a second pH adjusting step, a second extracting step and a second recovering step and may, if necessary, include other steps as well.

Detailed explanations of the first extracting step and the second extracting step will be omitted on the grounds that the first extracting step can employ a method similar to the above-mentioned method of the present invention for extracting at least one of palladium and platinum, and the second extracting step can employ a method similar to the above-mentioned method of the present invention for extracting zirconium.

<First pH Adjusting Step>

The first pH adjusting step is a step of adjusting the pH of an aqueous solution, which contains zirconium and at least one of palladium and platinum, in order to selectively extract at least one of the palladium and the platinum from the aqueous solution.

The pH of the aqueous solution at 25° C. is less than 3; it is particularly preferred that the pH be in the range of 1 to 2 in view of the fact that high selectivity for at least one of the palladium and the platinum is exhibited. When the pH is 8 or greater, it may be impossible to selectively extract at least one of the palladium and the platinum.

The method of measuring the pH is not particularly limited and may be suitably selected according to the intended purpose, and examples thereof include a measuring method which uses a pH meter (such as PH METER D-51, manufactured by HORIBA, Ltd.). Note that if the pH of the aqueous solution, which contains the zirconium and at least one of the palladium and the platinum, at 25° C. is already lees than 3 when measured, the above-mentioned first pH adjusting step may be omitted. Also, for adjustment of the pH, a method of adding an acid or an alkali may be employed as in the pH adjusting step in the above-mentioned method for extracting at least one of palladium and platinum.

<First Recovering Step>

The first recovering step is a step of recovering at least one of the palladium and the platinum from an organic phase obtained in the first extracting step.

The method for recovering at least one of the palladium and the platinum is not particularly limited and may be suitably selected according to the intended purpose, and examples thereof include a method wherein stirring or shaking in the first extracting step is stepped and a mixture of the organic phase and an aqueous phase is left to stand, thereby allowing the organic phase and the aqueous phase to separate from each other; subsequently, the organic phase that has separated is isolated from the aqueous phase by decantation or the like, then the isolated organic phase is brought into contact with another aqueous phase for recovery, thereby allowing metal(s) extracted into the organic phase to be inversely extracted and recovered in the aqueous phase for recovery.

The method for performing the inverse extraction is not particularly limited and may be suitably selected according to the intended purpose, and examples thereof include adjustment of the pH, temperature, etc. of the aqueous phase for recovery.

It is preferred that the aqueous phase for recovery be a solution containing an acid such as nitric acid, hydrochloric acid or sulfuric acid, and it is more preferred that this solution have a pH of 1 to 3.

<Second pH Adjusting Step>

The second pH adjusting step is a step of adjusting the pH of the aqueous solution from which at least one of the palladium and the platinum has been recovered, in order to selectively extract the zirconium from the aqueous solution.

The pH of the aqueous solution at 25° C. is 3 or greater, but less than 7; it is preferred that the pH be 3 or greater, but less than 5, particularly preferably in the range of 3.5 to 4.5, in view of the fact that high selectivity for the zirconium is exhibited. When the pH is less than 3, the extraction rate of the zirconium may be less than 60% and so the efficiency with which the zirconium is selectively extracted may be poor. When the pH is 7 or greater, metal(s) in the aqueous phase may precipitate, which is unsuitable for extracting conditions.

The method of measuring the pH is not particularly limited and may be suitably selected according to the intended purpose, and examples thereof include a measuring method which uses a pH meter (such as PH METER D-51, manufactured by HORIBA, Ltd.). Note that if the pH of the aqueous solution, which contains the zirconium, at 25° C. is already 3 or greater, but less than 7 when measured, the above-mentioned second pH adjusting step may be omitted. Also, for adjustment of the pH, a method of adding an acid or an alkali may be employed as in the pH adjusting step in the above-mentioned method for extracting zirconium.

<Second Recovering Step>

The second recovering step is a step of recovering the zirconium from an organic phase obtained in the second extracting step.

The method for recovering the zirconium is not particularly limited and may be suitably selected according to the intended purpose, and examples thereof include a method wherein stirring or shaking in the second extracting step is stopped and a mixture of the organic phase and an aqueous phase is left to stand, thereby allowing the organic phase and the aqueous phase to separate from each other; subsequently, the organic phase that has separated is isolated from the aqueous phase by decantation or the like, then the isolated organic phase is brought into contact with another aqueous phase for recovery, thereby allowing metal(s) extracted into the organic phase to be inversely extracted and recovered in the aqueous phase for recovery.

The method for performing the inverse extraction is not particularly limited and may be suitably selected according to the intended purpose, and examples thereof include adjustment of the pH, temperature, etc. of the aqueous phase for recovery.

It is preferred that the aqueous phase for recovery be a solution containing an acid such as nitric acid, hydrochloric acid or sulfuric acid, and it is more preferred that this solution have a pH of 1 to 3.

<Other Steps>

The above-mentioned other steps optionally contained in the metal recovering method are not particularly limited and may be suitably selected according to the intended purpose, and examples thereof include a step of confirming, by analysis, whether or not the zirconium or at least one of the palladium and the platinum has been recovered.

The analysis is not particularly limited and may be suitably selected according to the intended purpose, and examples thereof include analysis with an ICP emission analyzer or with an analyzer employing high-speed liquid chromatography, gas chromatography, ion chromatography, mass spectrometry, etc.

<Uses>

Since the metal recovering method enables zirconium and at least one of palladium and platinum to be selectively and highly efficiently recovered, the metal recovering method can be suitably used, for example, for recycling any of zirconium, palladium and platinum in view of stable supply of resources and protection of the environment.

(Method for Separately Extracting Palladium and Platinum)

A method of the present invention for separately extracting palladium and platinum includes a pH adjusting step, a palladium extracting step and a platinum extracting step and may, if necessary, include other steps as well.

<pH Adjusting Step>

The pH adjusting step is a step of adjusting the pH of an aqueous solution, which contains palladium and platinum, at 25° C.

In the case where the palladium and the platinum are to be selectively extracted, the pH of the aqueous solution at 25° C. is less than 7; it is preferred that the pH be less than 5, more preferably less than 3, particularly preferably in the range of 1 to 2, in view of the fact that high selectivity for the palladium and the platinum is exhibited. When the pH is 7 or greater, metal(s) in the aqueous phase may precipitate and thus it may be impossible to selectively extract the palladium and the platinum.

The method of measuring the pH is not particularly limited and may be suitably selected according to the intended purpose, and examples thereof include a measuring method which uses a pH meter (such as PH METER D-51, manufactured by HORIBA, Ltd.). Note that if the pH of the aqueous solution, which contains the palladium and the platinum, at 25° C. is already less than 7 when measured, the above-mentioned pH adjusting step may be omitted. Also, for adjustment of the pH, a method of adding an acid or an alkali may be employed as in the pH adjusting step in the above-mentioned method for extracting at least one of palladium and platinum.

<Palladium Extracting Step>

The palladium extracting step is a step of bringing a first organic phase, which contains at least an extractant having selectivity for the palladium, into contact with the aqueous solution, whose pH has been adjusted and which contains the palladium and the platinum, and selectively extracting the palladium into the first organic phase.

<<First Organic Phase>>

The first organic phase contains at least the extractant having selectivity for the palladium, preferably contains a solvent and may; if necessary, contain other components as well.

—Extractant Having Selectivity for Palladium—

The extractant having selectivity fox the palladium is not particularly limited, provided that it is capable of extracting the palladium, and the extractant may be suitably selected according to the intended purpose. Preference is given to the metal extractants mentioned in JP-A Nos. 2007-239066 and 2007-239088, and so forth. These may be used individually or in combination.

The concentration of the extractant, which has selectivity for the palladium, in the organic phase is not particularly limited and may be suitably selected according, for example, to the type of the extractant having selectivity for the palladium.

—Solvent—

The solvent preferably contained in the first organic phase is not particularly limited and may be suitably selected according to the intended purpose, and examples thereof include the solvent mentioned in relation to the above-mentioned method of the present invention for extracting at least one of palladium and platinum.

—Other Components—

The above-mentioned other components optionally contained in the first organic phase are not particularly limited and may be suitably selected according to the intended purpose. Also, the amounts of these other components are not particularly limited and may be suitably selected according to the intended purpose.

<<Extracting Method>>

The method of bringing the first organic phase into contact with the aqueous solution, which contains the palladium and the platinum, is not particularly limited and may be suitably selected according to the intended purpose, and examples thereof include a method of mixing a solution, which contains the first organic phase, with the aqueous solution, which contains the palladium and the platinum, and shaking or stirring the mixture. By such a method, the palladium can be selectively extracted from the aqueous solution containing the palladium and the platinum.

The speed and the length of time of the shaking, and the speed and the length of time of the stirring are not particularly limited and may be suitably selected according to the intended purpose; for example, they may be similar to those employed in the above-mentioned method of the present invention for extracting at least one of palladium and platinum.

<Platinum Extracting Step>

The platinum extracting step is a step of bringing a second organic phase, which contains at least the metal extractant of the present invention, into contact with the aqueous solution, which has undergone the palladium extracting step and contains the platinum, and extracting the platinum into the second organic phase.

Detailed explanations of the platinum extracting step will be omitted on the grounds that the platinum extracting step can employ a method similar to the above-mentioned method of the present invention for extracting at least one of palladium and platinum.

<Other Steps>

The above-mentioned other steps optionally included in the method for separately extracting palladium and platinum are not particularly limited and may be suitably selected according to the intended purpose, and examples thereof include a step of confirming, by analysis, whether or not the palladium and the platinum have been extracted, and a step of separately recovering the palladium and the platinum.

In the step of confirming, by analysis, whether or not the palladium and the platinum have been extracted, the analysis is not particularly limited and may be suitably selected according to the intended purpose, and examples thereof include analysis with an ICP emission analyzer or with an analyzer employing high-speed liquid chromatography, gas chromatography, ion chromatography, mass spectrometry, etc.

In the step of separately recovering the palladium and the platinum, the method for separately recovering the palladium and the platinum is not particularly limited and may be suitably selected according to the intended purpose, and examples thereof include a method wherein the palladium-containing organic phase obtained in the palladium extracting step and the platinum-containing organic phase obtained in the platinum extracting step are used and the palladium and the platinum are recovered as in the first recovering step in the above-mentioned metal recovering method of the present invention.

<Uses>

Since the method for separately extracting palladium and platinum enables palladium and platinum to be selectively and highly efficiently extracted, the method can be suitably used, for example, for separating palladium and platinum from each other in the above-mentioned method of the present invention for extracting at least one of palladium and platinum and the above-mentioned metal recovering method of the present invention, and the method can also be suitably used, for example, for recycling palladium and platinum in view of stable supply of resources and protection of the environment.

EXAMPLES

The following specifically explains the present invention, referring to Examples of the present invention. It should, however, be noted that the scope of the present invention is not confined to these Examples.

Production Example 1

Production of Cyclic Phenol Sulfide Intermediate Oligomer (A)

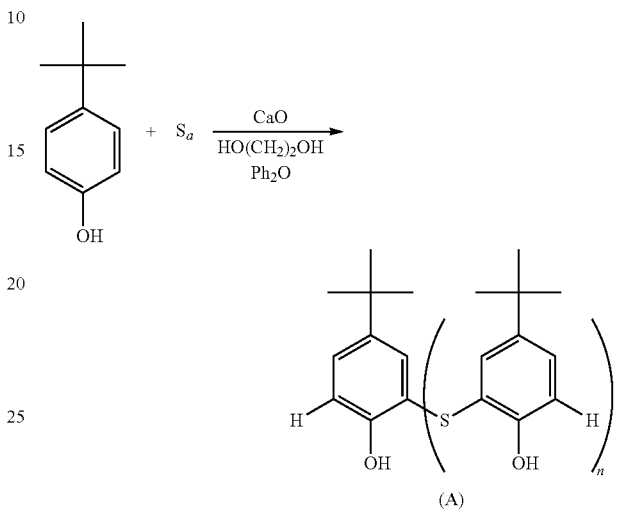

Into a 1,000 mL three necked flask, 300 g (2.0 mol) of p-tert-butylphenol, 64.0 mL of diphenyl ether ($Ph_2O$) and 56.0 mL (1.0 mol) of ethylene glycol were poured, and then heating and stirring were carried out in a nitrogen atmosphere; after the temperature had reached 60° C., 28.0 g (0.5 mol.) of calcium oxide was added, then the temperature was increased to 120° C. in approximately 20 minutes and the ingredients were reacted together for 2 hours. Thereafter, the ethylene glycol and produced water were distilled away under reduced pressure. To compensate for reduction in the amount of the diphenyl ether, which was also distilled away at the same time when the ethylene glycol and the water were distilled away under reduced pressure, diphenyl ether was added, then heating and stirring were again carried out in a nitrogen atmosphere; after the temperature had reached 100° C., 95.9 g (3.0 mol) of sulfur was added, then the temperature was increased to 230° C. and the ingredients were reacted together for 3 hours. Thereafter, cooling was carried out, and it was confirmed that the temperature had lowered to 110° C.; subsequently, 250 mL of toluene was gradually added to reduce the viscosity of the reaction liquid, and this reaction liquid was poured into 500 mL of 4N sulfuric acid to stop the reaction, Calcium sulfate deposited was filtered out, then the filtrate was washed with a saturated sodium sulfate aqueous solution, then concentrated and heated to 80° C. This filtrate was poured into 1 L of separately prepared acetic acid which had been heated to 80° C., then stirring was carried out at 80° C. for approximately 1 hour, and subsequently the mixture was left to stand overnight at room temperature. A precipitate deposited was washed with distilled water; thereafter, in order to remove unwashed acetic acid, the precipitate was dissolved in a large amount of chloroform, which was followed by washing with a sodium sulfate aqueous solution. Thereafter, the organic phase was dried with sodium sulfate, concentrated and then dried overnight under reduced pressure, and a cyclic phenol sulfide intermediate oligomer (A) was thus obtained. The yield rate of the cyclic phenol sulfide intermediate oligomer (A) was 67.8%.

Preparation Example 2

Production of Cyclic Phenol Sulfide (B)

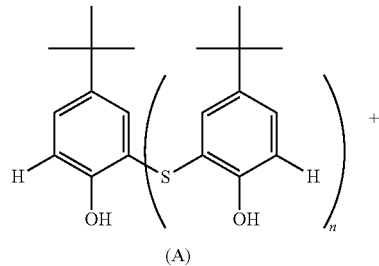

(A)

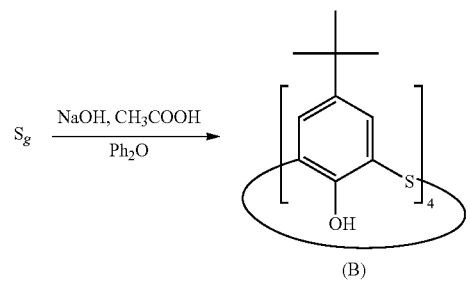

(B)

Into a 500 L three-necked flask, 30 g of the cyclic phenol sulfide intermediate oligomer (A) obtained in Production Example 1, 64.0 mL of diphenyl ether, 3.99 g of sodium hydroxide and 1.62 g of acetic acid were poured in this order, which was followed by heating and stirring in a nitrogen atmosphere, then 2.14 g of sulfur was fully added at 100° C., subsequently the temperature was increased to 230° C. in approximately 1 hour, and the ingredients were reacted together for 4 hours. Thereafter, cooling was carried out, toluene was added to reduce the viscosity of the reaction liquid, and 100 mL of 2N sulfuric acid was added to the reaction liquid to stop the reaction. After that, the aqueous phase was removed, which was followed by washing with a saturated sodium sulfate aqueous solution and subsequently with water, and afterward the mixed liquid was concentrated; thereafter, the diphenyl ether in the concentrated liquid was distilled away under reduced pressure. After that, the product was washed with acetone, a precipitate deposited was taken out by filtering and then dried under reduced pressure, and coarse crystals of a cyclic phenol sulfide were thus obtained. By dissolving these coarse crystals in chloroform to effect recrystallization, a cyclic phenol sulfide (B) was purified. The yield amount of the purified cyclic phenol sulfide (B) was 4.162 g, and the yield rate thereof was 13.90%.

Note that the cyclic phenol sulfide (B) (tetramer) and other multimers were separated from each other by the difference in solubility between them.

Production Example 3

Synthesis of Cyclic Phenol Sulfide Derivative (De-tert-butylated TC4A

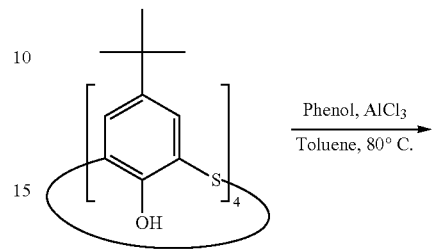

(B)

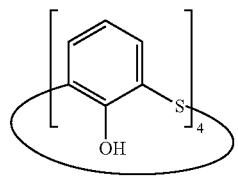

Into a 1,000 mL two-necked flask, 15.0 g (20.8 mmol) of the cyclic phenol sulfide (B) obtained in Production Example 2 was poured, then 450 mL of toluene was added, which was followed by stirring for 30 minutes, and the cyclic phenol sulfide (B) was thus dissolved in the toluene. Subsequently, 20.0 g (211.3 mmol) of phenol and 100 g (750.0 mmol) of aluminum chloride were added, and the ingredients were reacted together at 80° C. for 5 hours in a nitrogen stream. Thereafter, the reaction liquid was cooled to room temperature. In a 2,000 mL conical flask, 900 mL of 2N hydrochloric acid was placed, then the reaction liquid was slowly added with an ice bath, which was followed by overnight stirring at room temperature, and the aluminum chloride was thus deactivated. A precipitate obtained by this process was taken out by filtering, then pale yellow powder obtained was washed with 500 mL of water and subsequently with 500 mL of acetone; thereafter, a coarse product obtained by filtering was moved into a 500 mL conical flask, acetone was added, which was followed by stirring and then drying with a reduced-pressure dryer, and a cyclic phenol sulfide derivative (de-tort-butylated TC4A) in white powder form was thus obtained. The yield amount of the cyclic phenol sulfide derivative was 6.99 g, and the yield rate thereof was 68%.

Production Example 4

Synthesis of Cyclic Phenol Sulfide Derivative (Bromo TC4A)

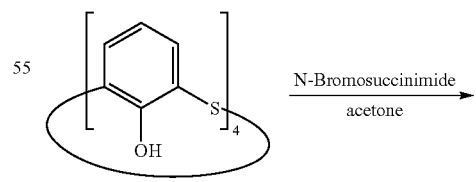

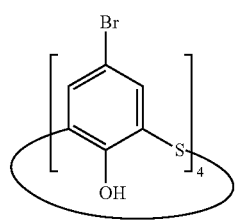

Into a 200 mL eggplant flask, 3.0 g (6.0 mmol) of the cyclic phenol sulfide derivative (de-tert-butylated TC4A) obtained in Production Example 3 and 60 mL of acetone were poured, then 6.74 g (32.0 mmol) of N-bromosuccinimide was added, and subsequently the ingredients were stirred at room temperature for 24 hours and thus reacted together. Thereafter, a precipitate was taken out by filtering and then washed with 20 mL of dichloromethane and subsequently with 20 mL of methanol, and a coarse product was thus obtained; this coarse product was washed with dichloromethane and subsequently with methanol and then dried under reduced pressure, and a cyclic phenol sulfide derivative (bromo TC4A) was thus obtained. The yield amount of the cyclic phenol sulfide derivative was 2.03 g, and the yield rate thereof was 41.7%.

Production Example 5

Synthesis of Cyclic Phenol Sulfide Derivative (Bromo TC4A Propyl Ether)

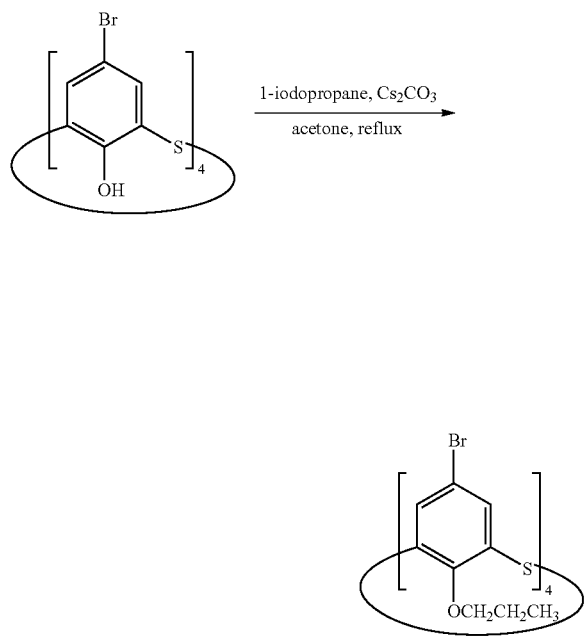

Into a 500 mL eggplant flask, 3.0 g (3.7 mmol) of the cyclic phenol sulfide derivative (bromo TC4A) obtained in Production Example 4, 7.2 g (22.0 mmol) of cesium carbonate and 200 mL of acetone were poured, then the ingredients were subjected to reflux (with heating) for 10 minutes. Subsequently, the ingredients were cooled to room temperature, then 5.1 g (30.0 mmol) of 1-iodopropane was added, and the ingredients were subjected to reflux (with heating) for 24 hours in a nitrogen stream and thus reacted together. Thereafter, the solvent was distilled away, then powder obtained was dissolved in chloroform, and washing with 100 mL of 2N hydrochloric acid and subsequently with 100 mL of water was carried out twice. The organic phase was isolated, then dried with anhydrous sodium sulfate and subsequently concentrated, and a coarse product was thus obtained. The obtained coarse product was purified by silica gel chromatography and dried under reduced pressure, and a cyclic phenol sulfide derivative (bromo TC4A propyl ether) in white powder form was thus obtained. The yield amount of the cyclic phenol sulfide derivative was 1.05 g, and the yield rate thereof was 28.6%.

Production Example 6

Synthesis of Cyclic Phenol Sulfide Derivative (Diphenylphosphino TC4A Propyl Ether)

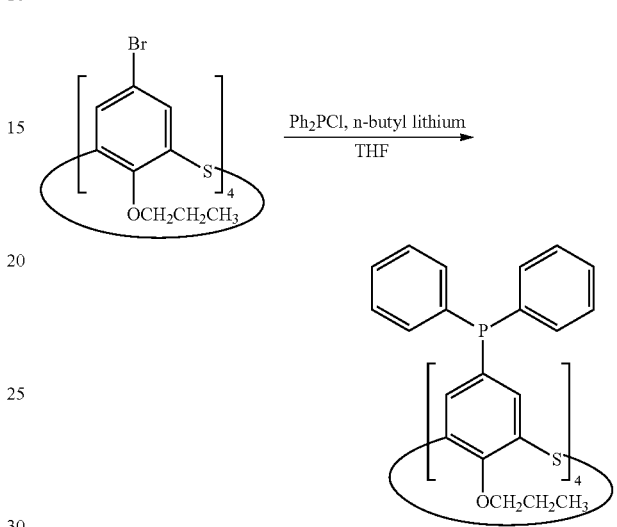

Into a 200 mL eggplant flask, 1.0 g (1.12 mmol) of the cyclic phenol sulfide derivative (bromo TC4A propyl ether) obtained in Production Example 5 and 60 mL of dehydrated tetrahydrofuran (THF) were poured, then the ingredients were cooled to −78° C. in a nitrogen stream; thereafter, 4.0 mL (6.28 mmol) of n-butyllithium (15% hexane solution) was added, and then stirring was carried out for 1 hour. After the stirring had finished, 2.0 g (9.06 mmol) of chlorodiphenylphosphine ($Ph_2PCl$) dissolved in 5 mL of tetrahydrofuran (THF) was added dropwise into the reaction liquid. After the dropwise addition thereof had finished, the temperature was increased to room temperature, then the ingredients were stirred for 2 hours and thus reacted together. Thereafter, the solvent was concentrated, and a coarse product was thus obtained. This coarse product was purified by silica gel column chromatography and dried under reduced pressure, and a cyclic phenol sulfide derivative (diphenylphosphino TC4A propyl ether) in white powder form as an objective product was thus obtained. The yield amount of the cyclic phenol sulfide derivative was 105 mg, and the yield rate thereof was 6.62%.

Example 1

Method for Extracting Palladium, Platinum, and Zirconium

—pH Adjusting Step—

Hydrochloric acid was added as an acid to an aqueous solution prepared by allowing waste matter, which contained several metals included in the 31 minerals defined by the Rare Metal Division of the Mineral Resources Subcommittee, Advisory Committee for Natural Resources and Energy of Ministry of Economy, Trade and Industry, to infuse with hydrochloric acid and hydrogen peroxide, and an aqueous solution having a pH of 1.6 at 25° C. was thus obtained. This aqueous solution was diluted 50-fold with distilled water (hereinafter, this diluted product will be referred to as "aqueous phase").

The metal concentrations of this aqueous phase, analyzed with an ICP emission analyzer (SPS3000, manufactured by Seiko Instruments Inc.), were as follows. Rh: 264.3 ppm, Pd: 737.8 ppm, Pt: 434.1 ppm, Zr: 198.2 ppm, Ce: >3,840.5 ppm, Ba: 2,118.2 ppm, Al: 2,272.5 ppm, La: 666.9 ppm, Y: 36.3 ppm.

—Extracting Step—

Into a sample tube (with a bore of 24.0 mm), 5 mL of an organic phase, prepared by dissolving the cyclic phenol sulfide derivative (diphenylphosphino TC4A propyl ether) synthesized in Production Example 6 in chloroform as a solvent such that the concentration of the cyclic phenol sulfide derivative became 2.92 mM, and 5 mL of the aqueous phase were poured, then stirring was carried out for 24 hours at room temperature and a stirring speed of 500 rpm with a stir bar (with a diameter of 14.0 mm).

—Measurement of Concentrations of Palladium, Platinum, and Zirconium—

The concentrations of the palladium, the platinum, and the zirconium in the aqueous phase were analyzed with an ICP emission analyzer, then, based upon the results of the analysis, the extraction rates (E %) of the palladium, the platinum, and the zirconium were calculated in accordance with Equation (I) below, The molar concentration ratio of the cyclic phenol sulfide derivative (diphenylphosphino TC4A propyl ether) to each of the palladium, the platinum, and the zirconium in the aqueous solution, measured with the ICP emission analyzer, was 1:1 (cyclic phenol sulfide derivative: Pd, Pt or Zr). The results are shown in FIG. 1 (Pd: shown by a white column, Pt: shown by a white column, Zr: shown by a white column) and Table 1.

$$(E\%) = (C_0 - C)/C_0 \times 100 \qquad \text{Equation (I)}$$

In Equation (I), "$C_0$" denotes the concentration (ppm) of a metal (Pd, Pt or Zr) in the aqueous phase before extraction, and "C" denotes the concentration (ppm) of the metal (Pd, Pt or Zr) in the aqueous phase after the extraction.

Example 2

Method for Extracting Palladium, Platinum, and Zirconium

Palladium, platinum, and zirconium were extracted in the same manner as in Example 1 except that the pH adjusting step was carried out as described below; subsequently, the concentrations of the palladium, the platinum, and the zirconium regarding Example 2 were measured as in Example 1. The results are shown in FIG. 1 (Pd: shown by a black column, Pt: shown by a black column, Zr: shown by a black column) and Table 1.

—pH Adjusting Step—

To the aqueous phase having a pH of 1.6 obtained in Example 1, 5 mol/L of a sodium hydroxide aqueous solution was added, and the pH of the aqueous phase was thus adjusted to 3.0.

When the concentrations of the palladium, the platinum, and the zirconium after each extracting step in Examples 1 and 2 were measured, the concentrations of the rhodium (Rh), the cerium (Ce), the barium (Ba), the aluminum (Al), the lanthanum (La) and the yttrium (Y) were also measured by analysis with an ICP emission analyzer as described above. The results are shown in FIG. 1 and Table 1.

TABLE 1

| pH at the time of extraction | Extraction rate (%) | | | | | | | | |
|---|---|---|---|---|---|---|---|---|---|
| | Rh | Pd | Pt | Zr | Ce | Ba | Al | La | Y |
| 1.6 | 4.22 | 93.1 | 64.4 | 37.3 | 2.98 | 2.71 | 0.96 | 2.92 | 0 |
| 3.0 | 2.62 | 92.9 | 66.2 | 100 | 3.69 | 2.69 | 0.54 | 5.87 | 0 |

FIG. 1 and Table 1 demonstrate that, under the low pH condition, by extracting the metals with the use of the metal extractant of the present invention, high extraction rates of the palladium and the platinum, which were 60% or above, were secured while the extraction rates of the rhodium, the cerium, the barium, the aluminum, the lanthanum and the yttrium were less than 10%, which means that high selectivity for the palladium and the platinum was exhibited and the palladium and the platinum could be extracted with high efficiency.

At a pH of 3.0 as well, high extraction rates of the palladium and the platinum, which were 60% or above, were secured while the extraction rates of the rhodium, the cerium, the barium, the aluminum, the lanthanum and the yttrium were less than 10%, and it was confirmed that the extraction rates of the metals were not dependent upon the pH. Meanwhile, the extraction rate of the zirconium at a pH of 1.6 was 37.3%, which was low, whereas the extraction rate of the zirconium at a pH of 3.0 was 100%.

Accordingly, the following has been found: the lower the pH of an aqueous solution containing palladium, platinum and zirconium is, the higher the extraction rates and the selectivity for the palladium and the platinum are; meanwhile, the higher the pH of the aqueous solution is, the higher the extraction rate of the zirconium is; thus, the metals, i.e., the palladium, the platinum and the zirconium, are selectively extracted.

Example 3

Metal Recovering Method

—First pH Adjusting Step—

Hydrochloric acid was added as an acid to an aqueous solution prepared by allowing waste matter, which contained several metals included in the 31 minerals defined by the Rare Metal Division of the Mineral Resources Subcommittee, Advisory Committee for Natural Resources and Energy of Ministry of Economy, Trade and Industry, to infuse with hydrochloric acid and hydrogen peroxide, and an aqueous solution having a pH of 1.6 at 25° C. was thus obtained. This aqueous solution was diluted 50-fold with distilled water (hereinafter, this diluted product will be referred to as "aqueous phase").

The metal concentrations of this aqueous phase, analyzed with an ICP emission analyzer (SPS3000, manufactured by Seiko Instruments Inc.), were as follows. Rh: 264.8 ppm, Pd: 737.8 ppm, Pt: 434.1 ppm, Zr: 198.2 ppm, Ce: >3,840.6 ppm, Ba: 2,118.2 ppm, Al: 2,272.5 ppm, La: 666.9 ppm, Y: 36.3 ppm, —First Extracting Step—

Into a sample tube (with a bore of 24.0 mm), 5 mL of an organic phase, prepared by dissolving the cyclic phenol sulfide derivative (diphenylphosphino TC4A propyl ether) synthesized in Production Example 6 in chloroform as a solvent such that the concentration of the cyclic phenol sulfide derivative became 2.92 mM, and 5 mL of the aqueous phase were poured, then stirring was carried out for 24 hours at room temperature and a stirring speed of 500 rpm with a stir bar (with a diameter of 14.0 mm).

—Measurement of Concentrations of Palladium, Platinum, and Zirconium—

The concentrations of the palladium, the platinum, and the zirconium in the aqueous phase were analyzed with an ICP emission analyzer, then, based upon the results of the analysis, the extraction rates (E %) of the palladium, the platinum, and the zirconium were calculated in accordance with Equation (I) below. The molar concentration ratio of the cyclic phenol sulfide derivative (diphenyphosphino TC4A propyl ether) to each of the palladium, the platinum, and the zirconium in the aqueous solution, measured with the ICP emission analyzer, was 1:1 (cyclic phenol sulfide derivative Pd, Pt or Zr), The results are shown in Table 2.

$$(E\%)=(C_0-C)/C_0\times100 \qquad \text{Equation (I)}$$

In Equation (I), "$C_0$" denotes the concentration (ppm) of a metal (Pd, Pt or Zr) in the aqueous phase before extraction, and "C" denotes the concentration (ppm) of the metal (Pd, Pt or Zr) in the aqueous phase after the extraction.

—First Recovering Step—

The organic phase obtained as a result of the first extracting step and separated and a hydrochloric acid aqueous solution were poured into a sample tube (with a bore of 24.0 mm), then stirring was carried out for 24 hours at room temperature and a stirring speed of 500 rpm with a stir bar (with a diameter of 14.0 mm). Thus, separation recovery took place as follows: the cyclic phenol sulfide derivative (diphenylphosphino TC4A propyl ether) was recovered in the organic phase, whereas the palladium and the platinum were recovered in the hydrochloric add aqueous solution.

—Second pH Adjusting Step—

To the aqueous phase obtained as a result of the first extracting step and separated, 5 mol/L of a sodium hydroxide aqueous solution was added, and the pH of the aqueous phase was thus adjusted to 3.0.

—Second Extracting Step—

Into a sample tube (with a bore of 24.0 mm), the aqueous phase, Whose pH had been adjusted to 3.0 in the second pH adjusting step, and an organic phase, prepared by dissolving the cyclic phenol sulfide derivative (diphenylphosphino TC4A propyl ether) synthesized in Production Example 6 in chloroform as a solvent such that the concentration of the cyclic phenol sulfide derivative became 2.92 mM, were poured, then stirring was carried out for 24 hours at room temperature and a stirring speed of 500 rpm with a stir bar (with a diameter of 14.0 mm).

—Measurement of Concentration of Zirconium—

The concentration of the zirconium was measured as in the measurement subsequent to the first extracting step. The results are shown in Table 2.

—Second Recovering Step—

The organic phase obtained as a result of the second extracting step and separated and a hydrochloric acid aqueous solution were poured into a sample tube (with a bore of 24.0 mm), then stirring was carried out for 24 hours at room temperature and a stirring speed of 500 rpm with a stir bar (with a diameter of 14.0 mm). Thus, separation recovery took place as follows: the cyclic phenol sulfide derivative (diphenylphosphino TC4A propyl ether) was recovered in the organic phase, whereas the palladium and the platinum were recovered in the hydrochloric acid aqueous solution.

TABLE 2

| Step | Result | |
|---|---|---|
| First pH adjusting step | pH: 1.6 | |
| First extracting step | Extraction rate of Pd | 93.1% |
| | Extraction rate of Pt | 64.4% |
| | Extraction rate of Zr | 37.3% |
| Second pH adjusting step | pH: 3.0 | |
| Second extracting step | Extraction rate of Zr | 100% |

In the present invention, since palladium, platinum and zirconium can be successively extracted by pH adjustment with one container alone, without changing a metal extractant, it is possible to simplify steps. Specifically, the following is possible: by using a metal extractant of the present invention together with an aqueous solution containing palladium, platinum and zirconium and using a known solvent extracting device, firstly the palladium and the platinum are highly selectively extracted at a pH of less than 3, the metal extractant is separated and recovered, mainly the palladium is recovered from the metal extractant by inversion extraction, then the pH of the aqueous solution is adjusted by addition of an alkali, the metal extractant is placed back in the aqueous solution, the zirconium is highly selectively extracted at a pH of 3 or greater, the metal extractant is separated and recovered, and mainly the zirconium is recovered from the metal extractant by inverse extraction.

A new compound, a metal extractant including the new compound and a method for extracting any of palladium, platinum and zirconium using the metal extractant, according to the present invention, enable any of palladium, platinum and zirconium to be selectively and highly efficiently extracted, and can therefore be suitably used, for example, for recycling any of palladium, platinum and zirconium in view of stable supply of resources and protection of the environment.

Also, by using the metal extractant of the present invention together with a solution containing at least one of palladium and platinum and also containing zirconium, it is possible to extract at least one of the palladium and the platinum first at a pH of, for example, approximately 1 and then extract the zirconium at an increased pH of, for example, approximately 3, and thus to recover the metals highly efficiently.

What is claimed is:

1. A compound represented by General Formula (1) below,

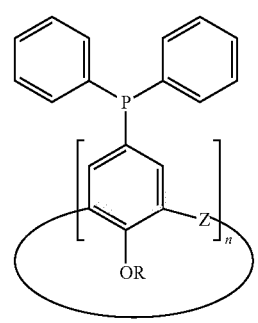

General Formula (1)

where R denotes a C1-C10 hydrocarbon group, Z denotes any one of a sulfide group, a sulfinyl group and a sulfonyl group, and n denotes an integer of 4 to 8.

2. The compound according to claim 1, wherein R denotes a propyl group.

3. The compound according to claim 1, wherein Z denotes a sulfide group.

4. The compound according to claim 1, wherein n denotes 4.

5. A metal extractant comprising:
a compound represented by General Formula (1) below,

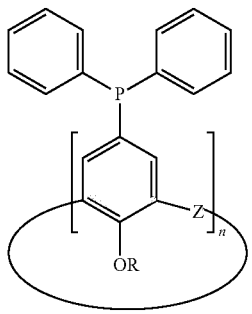

General Formula (1)

where R denotes a C1-C10 hydrocarbon group, Z denotes any one of a sulfide group, a sulfinyl group and a sulfonyl group, and n denotes an integer of 4 to 8.

6. A method for extracting at least one of palladium and platinum, comprising:
adjusting a pH of an aqueous solution, which contains at least one of palladium and platinum, at 25° C. to less than 7; and
bringing an organic phase, which contains at least a metal extractant comprising a compound represented by General Formula (1) below, into contact with the aqueous solution, whose pH has been adjusted and which contains at least one of the palladium and the platinum, and extracting at least one of the palladium and the platinum into the organic phase,

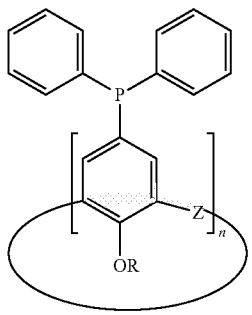

General Formula (1)

where R denotes a C1-C10 hydrocarbon group, Z denotes any one of a sulfide group, a sulfinyl group and a sulfonyl group, and n denotes an integer of 4 to 8.

7. A method for extracting zirconium, comprising:
adjusting a pH of an aqueous solution, which contains zirconium, at 25° C. to less than 7; and
bringing an organic phase, which contains at least a metal extractant comprising a compound represented by General Formula (1) below, into contact with the aqueous solution, whose pH has been adjusted and which contains the zirconium, and extracting the zirconium into the organic phase,

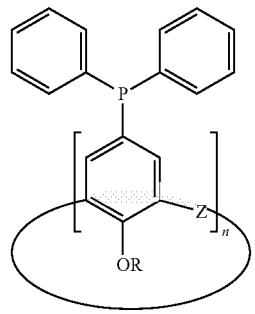

General Formula (1)

where R denotes a C1-C10 hydrocarbon group, Z denotes any one of a sulfide group, a sulfinyl group and a sulfonyl group, and n denotes an integer of 4 to 8.

8. A metal recovering method comprising:
adjusting a pH of an aqueous solution, which contains zirconium and at least one of palladium and platinum, at 25° C. to less than 3 as a first pH adjusting step;
bringing an organic phase, which contains at least a metal extractant comprising a compound represented by General Formula (1) below, into contact with the aqueous solution, whose pH has been adjusted in the first pH adjusting step, and extracting at least one of the palladium and the platinum into the organic phase as a first extracting step;
recovering at least one of the palladium and the platinum from the organic phase obtained in the first extracting step as a first recovering step;
adjusting the pH of the aqueous solution, which has undergone the first recovering step and contains the zirconium, to 3 or greater, but less than 7 as a second pH adjusting step;
bringing an organic phase, which contains at least the metal extractant, into contact with the aqueous solution, whose pH has been adjusted in the second pH adjusting step and which contains the zirconium, and extracting the zirconium into the organic phase as a second extracting step; and
recovering the zirconium from the organic phase obtained in the second extracting step as a second recovering step,

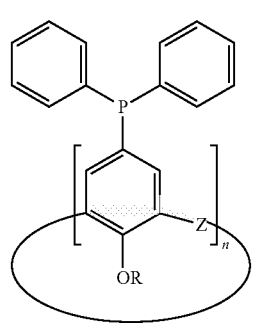

General Formula (1)

where R denotes a C1-C10 hydrocarbon group, Z denotes any one of a sulfide group, a sulfinyl group and a sulfonyl group, and n denotes an integer of 4 to 8.

9. A method for separately extracting palladium and platinum, comprising:
adjusting a pH of an aqueous solution, which contains palladium and platinum, at 25° C. to less than 7;

bringing a first organic phase, which contains at least an extractant having selectivity for the palladium, into contact with the aqueous solution, whose pH has been adjusted and which contains the palladium and the platinum, and extracting the palladium into the first organic phase; and bringing a second organic phase, which contains at least a metal extractant comprising a compound represented by General Formula (1) below, into contact with the aqueous solution, which has undergone the extraction of the palladium and contains the platinum, and extracting the platinum into the second organic phase, General Formula (1)

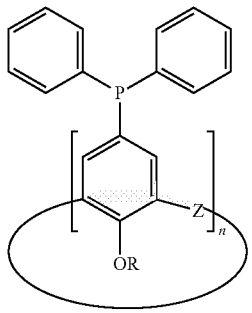

where R denotes a C1-C10 hydrocarbon group, Z denotes any one of a sulfide group, a sulfinyl group and a sulfonyl group, and n denotes an integer of 4 to 8.

* * * * *